US007640051B2

(12) United States Patent
Krishnan et al.

(10) Patent No.: US 7,640,051 B2
(45) Date of Patent: Dec. 29, 2009

(54) SYSTEMS AND METHODS FOR AUTOMATED DIAGNOSIS AND DECISION SUPPORT FOR BREAST IMAGING

(75) Inventors: Sriram Krishnan, Exton, PA (US); R. Bharat Rao, Berwyn, PA (US); Murat Dundar, Malvern, PA (US); Glenn Fung, Bryn Mawr, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1087 days.

(21) Appl. No.: 10/877,129

(22) Filed: Jun. 25, 2004

(65) Prior Publication Data
US 2005/0049497 A1 Mar. 3, 2005

Related U.S. Application Data

(60) Provisional application No. 60/482,293, filed on Jun. 25, 2003, provisional application No. 60/541,360, filed on Feb. 3, 2004.

(51) Int. Cl.
*A61B 5/00* (2006.01)
(52) U.S. Cl. .................. 600/407; 600/300; 382/128; 128/920; 128/922; 128/923; 128/924
(58) Field of Classification Search ............... 600/408; 378/37, 195; 382/128, 131, 132; 128/920, 128/922, 925
See application file for complete search history.

(56) References Cited

U.S. PATENT DOCUMENTS

| 5,235,510 | A | 8/1993 | Yamada et al. |
| 5,487,387 | A | 1/1996 | Trahey et al. ......... 128/660.02 |
| 5,622,171 | A | 4/1997 | Asada et al. |
| 5,732,697 | A | 3/1998 | Zhang et al. ............. 128/630 |
| 5,769,074 | A | 6/1998 | Barnhill et al. ........... 128/630 |
| 5,984,870 | A | * 11/1999 | Giger et al. .............. 600/443 |
| 6,058,322 | A | * 5/2000 | Nishikawa et al. ......... 600/408 |

(Continued)

OTHER PUBLICATIONS

Kates R et al: "Prospects for clinical decision support in breast cancer based on neural network analysis of clinical survival data" Knowledge-Based Intelligent Engineering Systems and Allied Technologies, 2000. Proceedings. Fourth International Conference on Brighton, UK Aug. 30-Sep. 1 vol. 2, Aug. 30, 2000, pp. 764-767, XP010523710 ISBN: 0-7803-6400-7 abstract; figures 1-3 paragraphs Introduction!, Patient!, Data!

(Continued)

*Primary Examiner*—Long V Le
*Assistant Examiner*—Vani Gupta (57) ABSTRACT

CAD (computer-aided diagnosis) systems and applications for breast imaging are provided, which implement methods to automatically extract and analyze features from a collection of patient information (including image data and/or non-image data) of a subject patient, to provide decision support for various aspects of physician workflow including, for example, automated diagnosis of breast cancer other automated decision support functions that enable decision support for, e.g., screening and staging for breast cancer. The CAD systems implement machine-learning techniques that use a set of training data obtained (learned) from a database of labeled patient cases in one or more relevant clinical domains and/or expert interpretations of such data to enable the CAD systems to "learn" to analyze patient data and make proper diagnostic assessments and decisions for assisting physician workflow.

38 Claims, 5 Drawing Sheets

U.S. PATENT DOCUMENTS

| | | | |
|---|---|---|---|
| 6,317,617 | B1 | 11/2001 | Gilhuijs et al. |
| 7,203,350 | B2 * | 4/2007 | Leichter et al. ............. 382/128 |
| 2002/0065466 | A1 | 5/2002 | Rather et al. |

OTHER PUBLICATIONS

Drukker Karen et al: "Computerized lesion detection on breast ultrasound" Medical Physics, American Institute of Physics. New York, US, vol. 29, No. 7, Jul. 2002, pp. ISSN: 0094-2405 abstract paragraphs 00II!, 00IV!

Acciani G et al: "Validation of neural network analysis to predict prognosis in breast cancer patients" Circuits and Systems, 1993., Proceedings of the 36$^{th}$ Midwest Symposium on Detroit, MI, USA Aug. 16-18, 1993, New York, NY, USA IEEE, pp. 453-456, XP010119707 ISBN: 0-7803-1760-2 the whole document.

Lisboa P J G et al: "Survival of breast cancer patients following surgery: a detailed assessment of the multi-layer perception and Cox's proportional hazard model" Neural Networks Proceedings, 1998. IEEE World Congress on Computational Intelligence. The 1998 IEEE International Joint Conference on Anchorage, AK, USA 4-9 vol. 1, May 4, 1998, pp. 112-116, XP010286530 ISBN: 0-7803-4856-1 p. 122 p. 115; figures 1,2,5,6.

International Search Report, Mar. 15, 2005.

* cited by examiner

SYSTEMS AND METHODS FOR AUTOMATED DIAGNOSIS AND DECISION SUPPORT FOR BREAST IMAGING

CROSS-REFERENCE TO RELATED APPLICATION

This application claims priority to U.S. Provisional Application Ser. No. 60/482,293, filed on Jun. 25, 2003, and U.S. Provisional Application Ser. No. 60/541,360, filed on Feb. 3, 2004, both of which are fully incorporated herein by reference.

TECHNICAL FIELD OF THE INVENTION

The present invention relates generally to systems and methods for providing automated diagnosis and decision support for medical imaging and, in particular, to CAD (computer-aided diagnosis) systems and applications for breast imaging, which use machine-learning techniques that enable such systems and application to "learn" to analyze parameters extracted from image data and/or non-image patient data of a subject patient for purposes of providing automated decision support functions to assist a physician in various aspects of physician workflow including, but not limited to, diagnosing medical conditions (breast tumors) and determining efficacious healthcare or diagnostic or therapeutic paths for the subject patient.

BACKGROUND

Today, in most countries, women over a certain age (usually 40) are screened for breast cancer using X-ray mammography. If the results of the X-ray mammography present suspicious or potentially cancerous breast tissue, the patient is sent for a diagnostic workup. Alternatively, the patient can be sent for a diagnostic workup through other paths, such as the result of a physical examination in which the examining physician feels or otherwise identifies some abnormal feature (e.g., lump) in a patient's breast, or in circumstance in which the patient has an extremely high risk of cancer as determined through the patient's clinical, history, or other means.

In a diagnostic workup, the patient's breasts will be imaged with one of several imaging modalities, including X-ray mammography (digital or analog), MRI, or ultrasound, for the purposes of screening or evaluating for anatomical abnormalities in breast tissue including microcalcifications or masses in breast tissue, and various other lesions or abnormalities that are potentially cancerous. Newer techniques are also being developed for diagnostic purposes, including X-ray tomosynthesis, optical imaging, strain imaging, nuclear imaging, etc, which can be used to obtain diagnostic images of the patient's breast for evaluation by the physician determine whether a particular lesion in breast tissue is benign or malignant.

After reviewing a diagnostic image, if the physician believes that a lesion may be malignant, a biopsy will be performed to remove a piece of the lesion tissue for analysis. This process is assumed to be a "gold standard" for characterization of benign or malignant tissue. However, it is preferable to minimize the number of biopsies that are performed for various reasons. For instance, a biopsy procedure causes pain and scarring for the patient, and the long period of time between the time of the biopsy procedure and the time the results are provided to the patient (usually at least a few days), the patient may be become severely stressed in anticipation of potentially obtaining negative results. On the other hand, biopsy procedures enable physicians to accurately diagnose a large percentage of patients with breast cancer. Thus, there is some trade-off or balance between sensitivity and specificity that is typically maintained.

In the field of medical imaging, although various imaging modalities and systems can be used for generating diagnostic images of anatomical structures for purposes of screening and evaluating medical conditions, with respect to breast cancer detection, each diagnostic imaging modality has its own advantages and disadvantages, and the optimal choice of imaging modality may not be the same for every patient. Ideally, the imaging modality for a given patient is selected to maximize sensitivity and specificity for the patient. For each patient, there may be one or more "optimal" imaging modalities for such purpose. Unfortunately, due to cost, it is not possible to image every patient using multiple imaging modalities, and then choose which modality would provide the optimal balance between sensitivity and specificity.

The choice of diagnostic imaging modality is usually made by the referring physician based on a number of factors, including, for example, (i) availability and cost, (ii) comfort level and experience of the referring physician, or (ii) a physician's "gut feeling" as to which imaging modality would be optimal to obtain information for the patient. While the first factor is unavoidable, the second and third factors can lead to a sub-optimal choice of imaging modality for the individual patient.

SUMMARY OF THE INVENTION

Exemplary embodiments of the invention generally include systems and methods for providing automated diagnosis and decision support for breast imaging. More specifically, exemplary embodiments of the invention include CAD (computer-aided diagnosis) systems and applications for breast imaging, which implement automated methods for extracting and analyzing relevant features/parameters from a collection of patient information (including image data and/or non-image data) of a subject patient to provide automated assistance to a physician for various aspects of physician workflow in breast care. For example, a CAD system can provide automated diagnosis of breast cancer and other related conditions, assessments with regard to the risk of a subject patient having breast cancer and/or developing breast cancer in the future, and other automated decision support functions to assist a physician in determining efficacious healthcare or diagnostic or therapeutic paths for a subject patient based on a current state of the patient.

In other exemplary embodiments of the invention, CAD systems and methods for breast imaging implement machine-learning techniques which use training data that is obtained (learned) from a database of previously diagnosed (labeled) patient cases in one or more relevant clinical domains and/or expert interpretations of such data to enable the CAD systems to "learn" to properly and accurately analyze patient data and make proper diagnostic and/or therapeutic assessments and decisions for assisting physician workflow.

These and other exemplary embodiments, features and advantages of the present invention will be described or become apparent from the following detailed description of exemplary embodiments, which is to be read in connection with the accompanying drawings.

DETAILED DESCRIPTION OF EXEMPLARY EMBODIMENTS

In general, exemplary embodiments of the invention as described below include systems and methods for providing automated diagnosis and decision support for breast imaging. More specifically, exemplary embodiments of the invention as described below with reference to FIGS. 1~4, for example, include CAD (computer-aided diagnosis) systems and applications for breast imaging, which implement automated methods for extracting and analyzing relevant features/parameters from a collection of patient information (including image data and/or non-image data) of a subject patient to provide automated assistance to a physician for various aspects of physician workflow including, for example, automated assistance to a physician for various aspects of physician workflow where decisions must be made respecting healthcare or diagnosis paths and/or therapeutic paths for the patient. Various methods have been developed which attempt to provide decision support for physicians using only information from images. However, these techniques ignore the fact that there is a significant amount of information contained in the patient record in the form of non-image data. Advantageously, as described in detail below, CAD systems and methods according to exemplary embodiments of the invention provide automated decision support methods that combine both imaging and non-imaging data. Here, non-imaging data is taken to include all information found in a patient's record other than images, which can include but not be limited to, demographic data, history and physical information, physician notes, lab results, results from blood tests, results from proteomic analysis, and results from genetic assays. For example, in the specific case of breast imaging, two women with identical images with suspicions findings may be treated differently if, for example, one patient is a young woman with no history or risk factors for cancer, while the other patient is an elderly woman with genetic disposition for breast cancer (such as the presence of the BRCA gene) and a known family history of breast cancer. Combining the clinical and imaging information provides the most valuable assistance for the physician.

For instance, given a set of information that is collected for a given patient, CAD systems according to exemplary embodiments of the invention can extract and analyze relevant features from such patient information to automatically assess the current state of the patient (e.g. probability and confidence of diagnosis of a disease or a likelihood of having a particular disease given history, age, etc.), automatically determine which additional test(s) or features(s), if any, would be useful to increase the confidence in a diagnosis, and otherwise provide decision support to a physician in other aspects of physician workflow.

Exemplary CAD systems and applications according to the invention implement machine-learning techniques that use training data obtained (learned) from a database of labeled patient cases in one or more relevant clinical domains and/or expert interpretations of such data to enable the CAD systems to "learn" to properly and accurately analyze patient data and make proper diagnostic assessments and decisions for assisting physician workflow. For example, with respect to breast imaging a diagnosis of breast cancer, exemplary CAD systems described below can "learn" to provide proper assessments in the areas of screening, diagnosis and/or staging of breast cancer. For illustrative purposes, exemplary embodiments of the invention will be described with specific reference to breast imaging and physician workflow for breast care. It is to be understood, however, that the present invention is not limited to any particular medical fields. Rather, the invention is more generally applicable to any medical field of practice in which physician workflow requires the physician to determine or assess the current state of a patient and determine workflow paths would result in a more accurate assessment of the current state of the patient for purposes of providing the appropriate care. Those of ordinary skill in the art will readily appreciate that CAD systems according to exemplary embodiments of the invention provide a powerful tool to assist physician workflow.

It is to be understood that the systems and methods described herein in accordance with the present invention may be implemented in various forms of hardware, software, firmware, special purpose processors, or a combination thereof. In one exemplary embodiment of the invention, the systems and methods described herein are implemented in software as an application comprising program instructions that are tangibly embodied on one or more program storage devices (e.g., magnetic floppy disk, RAM, CD Rom, DVD, ROM and flash memory), and executable by any device or machine comprising suitable architecture, wherein the application may be a distributed network application with n-tier client-server architecture for a distributed network application, etc.

It is to be further understood that because the constituent system modules and method steps depicted in the accompanying Figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

Figure 1:
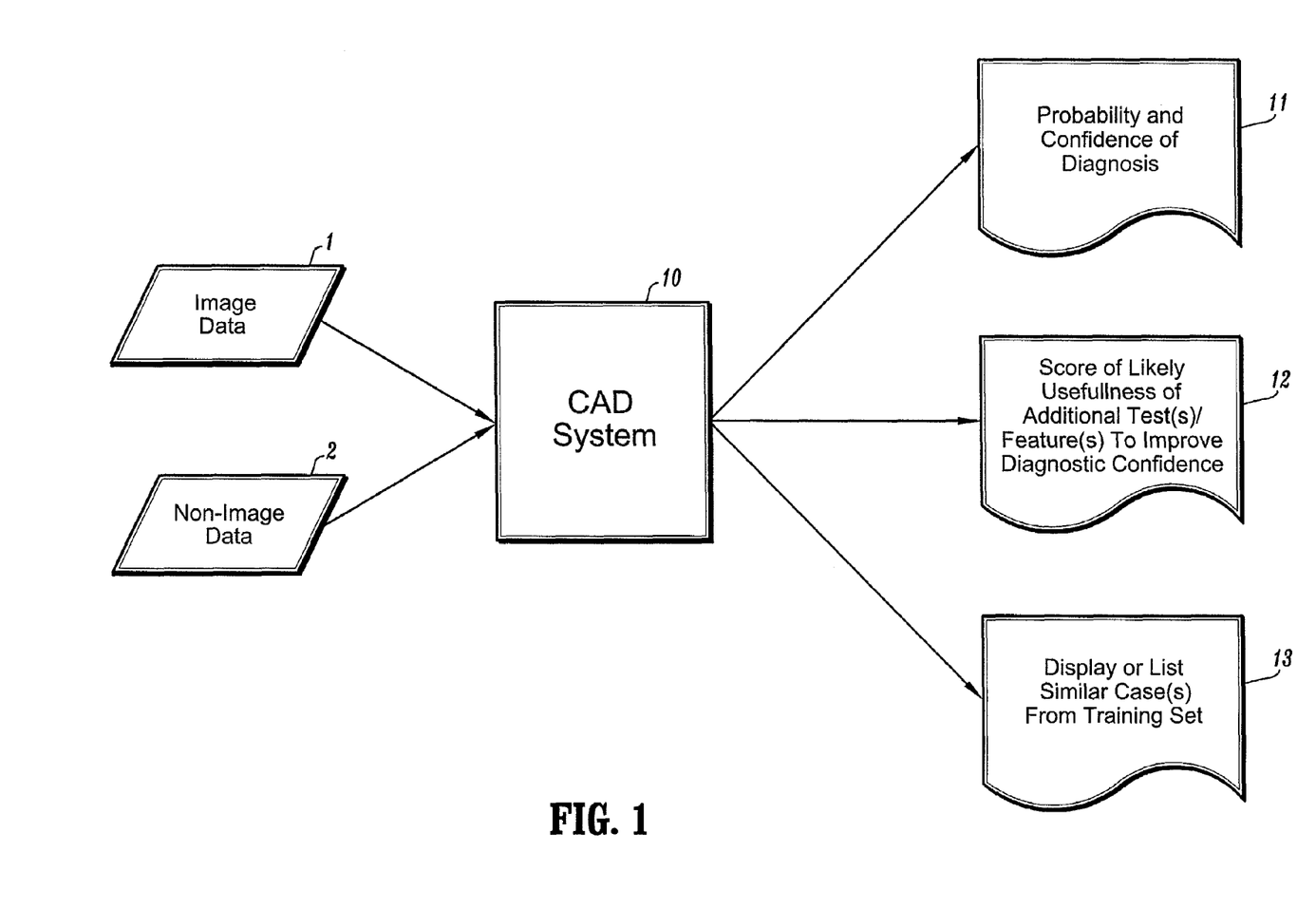
FIG. 1 is a block diagram of a system for providing automatic diagnostic and decision support for breast imaging according to an exemplary embodiment of the invention.

FIG. 1 is a high-level block diagram of a system for providing automated diagnostic support and physician workflow assistance for breast imaging, according to an exemplary embodiment of the invention. More specifically, FIG. 1 illustrates a CAD (computer-aided diagnosis) system (10) that implements methods for analyzing various types of patient information (1) and (2) of a subject patient to provide diagnostic assessments and recommendations and other decision support to assist a physician in various aspects of physician workflow with respect to the subject patient. The CAD system (10) uses machine learning methods that enable the CAD system (10) to continually learn to analyze the patient information (1, 2) and continually provide more accurate diagnostic assessments and/or decisions to assist physician workflow.

The input to the CAD system (10) comprises various sources of patient information including image data (1) in one or more imaging modalities (e.g., ultrasound image data, X-ray mammography image data, MRI etc.) and non-image data (2) from various structured and/or unstructured data sources, including clinical data which is collected over the course of a patient's treatment and other information such as patient history, family history, demographic information, financial information, and any other relevant patient information. The CAD system (10) implements methods for automatically extracting information (features) from the image data (1) and non-image data (2) and combining the extracted information in a manner that is suitable for analysis by the CAD system (10). Depending on the diagnostic and decision support function(s) supported by the CAD system (10), the CAD system (10) can generate one or more outputs (11), (12), and/or (13). As explained below, in the field of breast care, these outputs can provide physician workflow assistance in the areas of screening, diagnosing and/or staging for breast cancer.

In another exemplary embodiment of the invention, the CAD system (10) can extract and analyze information from image data (1) and (optionally) non-image data (2) to automatically generate and output a probability of diagnosis and (optionally) a measure of confidence of the diagnosis (11) or alternatively output a suggested therapy with a probability and (optional) measure of confidence as to the impact of the suggested therapy, e.g., the probability that the suggested therapy will have the desired (beneficial) impact. Collectively, the output (11) can be referred to herein as "Probability and Confidence of Suggestion".

More specifically, by way of example, for purposes of diagnosing breast cancer, the CAD system (10) may comprise methods for automatically detecting and diagnosing (or otherwise characterizing) suspect breast lesions in breast tissue and outputting, for example, a probability of malignancy of such lesions, together with an optional measure of confidence in such diagnosis. In this example, the CAD system (10) could extract and analyze relevant features from a screening X-ray mammogram (image data) and clinical history information (non-image data) of a patient and provide a current estimate and confidence of malignancy.

Alternatively, for patients with known breast cancer for example, the CAD system (10) could suggest an course of therapy, in which case, the probability and confidence (11) would refer to the likelihood that the therapy would have the desired (presumably beneficial) impact, which could range from curing the patient from breast cancer, to a purely palliative treatment whose sole aim would be to improve the quality of life of a patient with terminal breast cancer. More specifically, the CAD system (10) could in addition to suggesting a therapy, automatically provide a probability and/or measure of confidence that the therapy will have a determined outcome and possible provide a probability and/or measure of confidence that the therapy will not have a determined detrimental impact such as side effects. The probability can be specified as a distribution over possible outcomes both beneficial and detrimental, or a set of distributions over possible outcomes both beneficial and detrimental at one or more time points in the future, or a time-varying distribution over possible outcomes at different times in the future, etc.

In another exemplary embodiment of the invention, the CAD system (10) can automatically determine and specify one or more additional tests, measurements, or features which, if made/obtained, could increase the confidence of diagnosis (i.e., sensitivity analysis). For example, the CAD system (10) can determine and output a "score" (12) for each additional test, measurement or feature, which provides some measure or indication as to the potential usefulness of the particular imaging modality or feature(s) that would improve the confidence of an assessment or diagnosis determined by the CAD system (10). For example, assuming the CAD system (10) extracts and analyzes relevant features from a screening X-ray mammogram (image data) and clinical history information (non-image data) of a patient and provides a current estimate and confidence of malignancy of a detected lesion, the CAD system (10) could further indicate which imaging modality or modalities would most likely provide the maximum amount of additional information that would be useful in determining whether the lesion is malignant or benign, or determining the extent of cancer ("staging"), or would be most useful in deciding on a course of therapy for a patient with known breast cancer—for instance, deciding between surgery, radiotherapy, chemotherapy, hormone therapy or some combination thereof (the so called "cocktail" therapy).

In another exemplary embodiment of the invention, the CAD system (10) can identify and output (via display or list) one or more exemplary case studies that are similar to a current case (13). For example, as noted above and explained in further detail below, the CAD system (10) may comprise a database (or library) of previously labeled (diagnosed) cases, and based on features extracted from patient information input to the CAD system (10) for the subject patient, the CAD system (10) can search and display the n-most relevant cases from the library for diagnostic assistance. In other words, the CAD system (10) can provide a set of similar cases from the training set using the automatically extracted features.

It is to be appreciated that the CAD system (10) function of displaying similar cases in the context of physician workflow can provide significant assistance to the physician. For instance, displaying similar cases can provide training for inexperienced users. Indeed, novice users can review other cases to determine or otherwise understand the basis or reasons why the case interpreted in the way that it was. Moreover, display of similar cases can provide a means for experienced users to confirm the diagnostic results of the CAD system (10). Indeed, in addition to probability of diagnosis for a given condition, the CAD system (10) could display similar cases to justify its assessment. Moreover, displaying similar cases enables assessment of prognosis and treatment. More specifically, by studying similar cases to see how other patients responded to different treatment options, a physician can begin to assess the efficacy of these options for the current patient.

In view of the above, the CAD system (10) can be generally viewed as an automated system that can assist physician workflow by providing an assessment of the current state of a patient (e.g. probability of likelihood of a particular disease) and determining next best health care or diagnostic paths for the subject patient (e.g., identifying additional tests (or features) that can be obtained, which would likely reduce any ambiguity of the assessment). As noted above, it is to be appreciated that the CAD system (10) implements one or more machine-learning methods whereby the information is learned, and the decisions driven, by data that is collected in a training set of the CAD system (10). In particular, as noted above, the CAD system (10) could include a library of exemplary diagnosed cases from which training data is obtained to teach the CAD system (10). In contrast to "expert systems" which are developed and derived from a set of rules dictated by an expert and translated into code, the CAD system (10) learns to provide accurate diagnostic decisions and provide decision support based on training data that is learned from diagnosed cases or learned from expert knowledge.

It is to be appreciated that various machine learning methods may be implemented by the CAD system (10). For example, the systems and methods described in U.S. patent application Ser. No. 10/702,984, filed on Nov. 6, 2003, by Zhou et al, entitled "System and Method for Real-Time Feature Sensitivity Analysis Based on Contextual Information,"

which is commonly assigned and incorporated herein by reference, can be used in the CAD system (10) for determining which tests or features may be most relevant for reducing ambiguity of a diagnosis. Essentially, the Zhou approach is to create a model of the process, and determine the relative importance of each feature in reducing ambiguity. Such method can be implemented herein whereby each imaging modality, or diagnostic path, could be described as a set of one or more features. Then, the methods described by Zhou would be used to determine which feature(s) would likely provide the greatest improvement in confidence in a diagnosis or assessment. Other machine learning techniques which learn from a large training set of cases can be implemented in the CAD system (10). For example, various machine learning techniques, such as decision trees, SVM, neural networks, or Bayesian networks, or ensemble methods which combine multiple such methods, for example, may be used. Alternately, model-based algorithms which would be defined or trained specifically to detect some kind of lesion, for instance, based on causal knowledge of the various factors that are related to a particular kind of lesion, for example.

It is to be appreciated that the CAD system (10) can provide proper decision support even in the absence of various features or information that can be used for rendering such decisions. For example, if the medical records of a patient only contain a screening mammogram and basic demographic information about the patient (for example, age and race), but no clinical or family information, the CAD system (10) is able to provide a probability and confidence of diagnosis, along with a best estimation of what test or procedure should be performed next. In this case, the recommended procedure might even be to collect the family information for the patient. Of course, the confidence of the system will improve with more information as it is provided. As an extreme, consider the situation where there no information at all for a given patient. In this instance, the CAD system (10) should be able to provide a physician with some guidance as to an initial step to take with respect to the patient. Various methods for learning and/or performing inference with missing/noisy data may be used in the decision support system.

It is to be appreciated that the above methods can be extended to provide automatic screening for medical conditions such as breast cancer. In the United States, current recommendations provide that all women over the age of 40 are to be screened yearly using X-ray mammography. As in the case of breast cancer diagnosis, there have been studies in the literature to automatically assess the risk associated with mammograms. In this regard, it may be that MRI or ultrasound may be better screening tools for a particular subset of the population or for women with some particular finding in their diagnostic mammogram. Furthermore, for some women, the risk of developing breast cancer at the current point in their life may be so small that it may not be worth the risk of being subjected to ionizing radiation, or the cost, to even perform a screening.

Accordingly, the CAD system (10) can be configured to make a determination, in view of a patient's clinical and family history, as to the likelihood that the patient has (or can develop) breast cancer, and what screening test (if any) should be given to the patient to best detect suspicious lesions or risk of cancer for further diagnosis. This likelihood could also be inferred at any point in time during the patient history, e.g., after the first screening exam, or after multiple screens and MRI tests. Such determinations can be made using a training set as described above and using machine-learning techniques. Moreover, for screening, the CAD system (10) can generate and output decisions as discussed above, including likelihood of disease, exemplar cases from a training set, and the screening test that would be optimal for the given patient. In this case, a determination as to the screening test may be of most interest. Indeed, for such determination, a screening mammogram would not be available for the classification. Moreover, the comparison would not necessarily be made to correct a diagnosis of the patient, but rather to correct identification of either suspicious lesions in the breast, or sufficient risk of breast cancer to warrant further diagnostic tests.

In another exemplary embodiment of the invention, the CAD system (10) can provide assistance in breast imaging with regard to staging of tumors for therapy. In general, a staging process involves precisely locating a lesion and determining if a lesion is single- or multi-focal. In according the an exemplary embodiment of the invention, the CAD system (10) can learn to determine which test should be used to stage a lesion, given information about the lesion obtained from screening and/or diagnosis test. For example, in a training set, the results of the staging from different modalities could be compared to those results actually found during therapy or follow-up visits. Accordingly, machine-learning methods as described above can be used to enable the CAD system (10) to "learn" a proper approach to staging for a given patient. Exemplar cases from the training set can also potentially show what the results of the staging, and perhaps even the outcomes after therapy for patients with "similar" cases.

Figure 2:
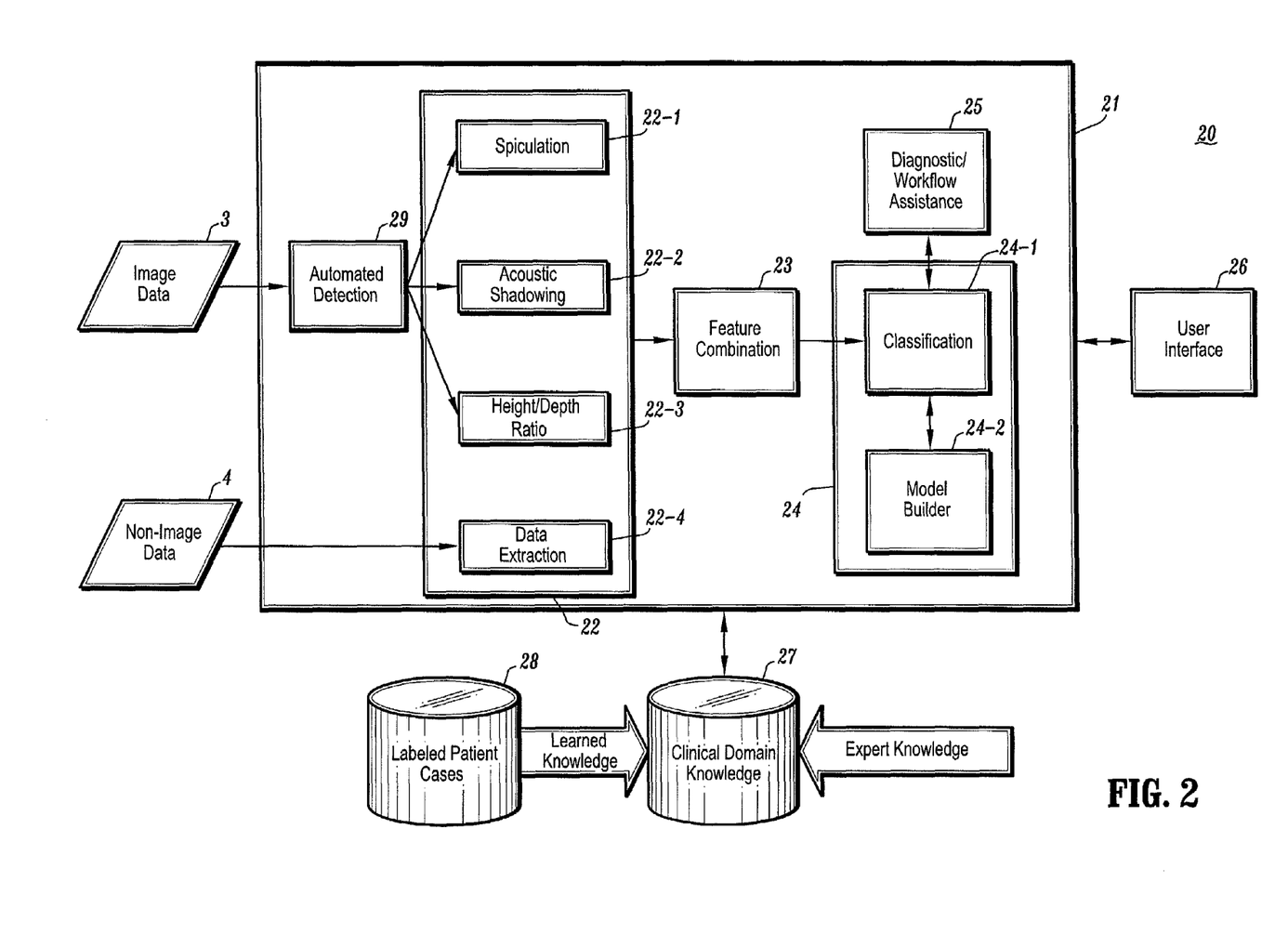
FIG. 2 is a block diagram of a system for providing automatic diagnostic and decision support for breast imaging according to another exemplary embodiment of the invention.
Figure 3:
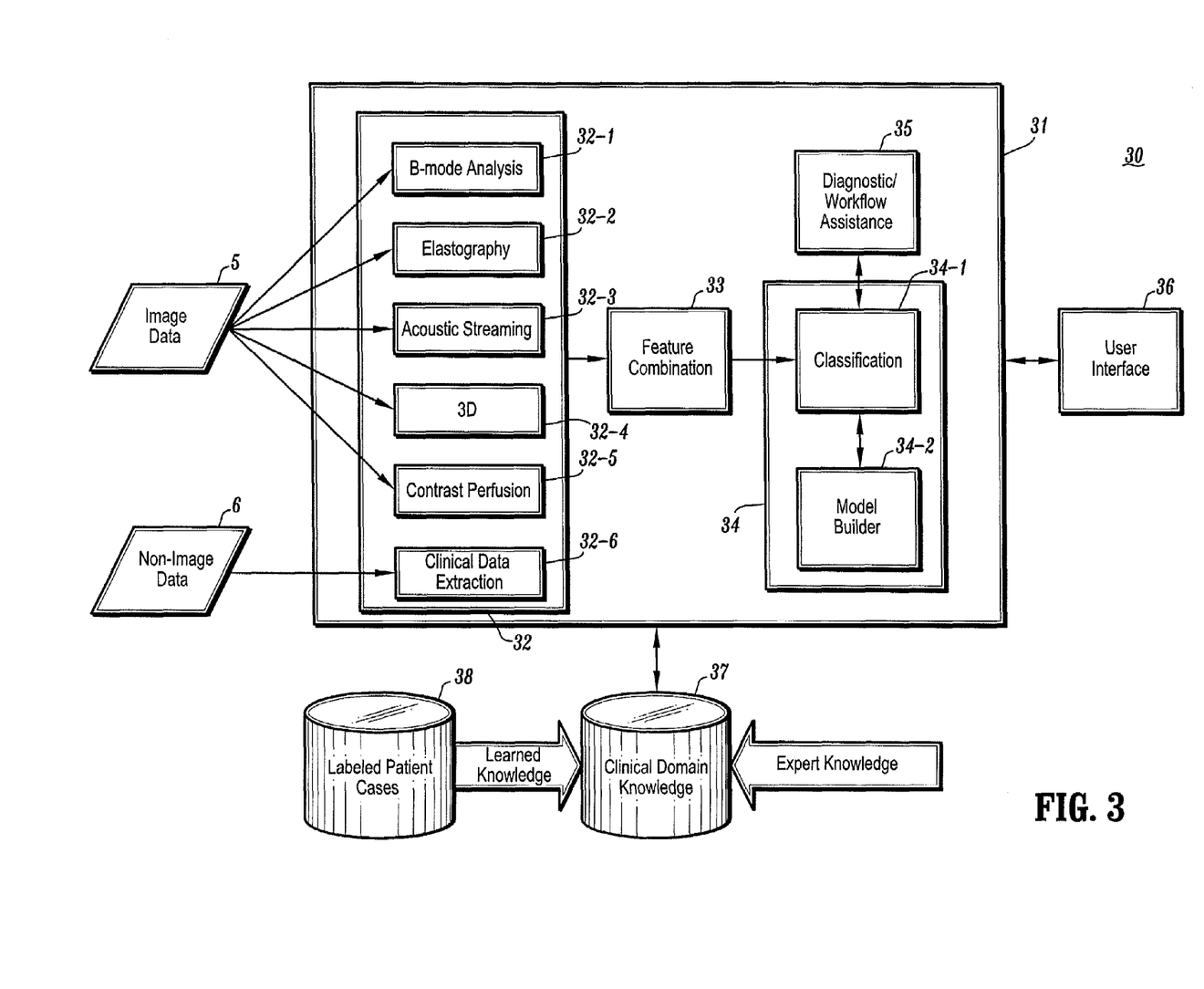
FIG. 3 is a block diagram of a system for providing automatic diagnostic and decision support for breast imaging according to another exemplary embodiment of the invention.
Figure 4:
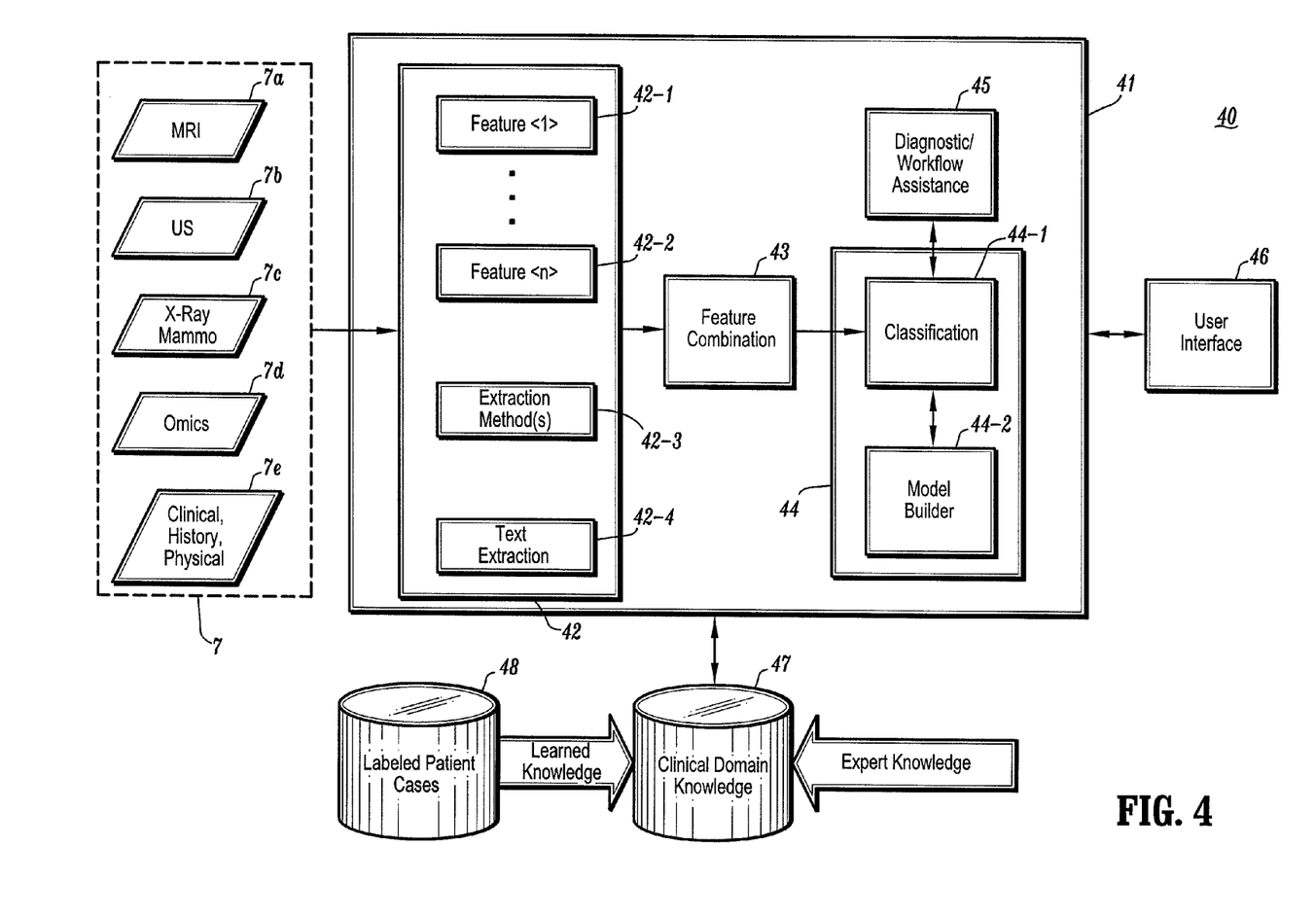
FIG. 4 is a block diagram of a system for providing automatic diagnostic and decision support for breast imaging according to another exemplary embodiment of the invention.

The exemplary CAD systems and methods discussed above with reference to FIG. 1 provide a general framework for developing CAD systems that can support one or more imaging modalities and provide one or more functionalities for providing assistance in various aspects of physician workflow. Exemplary embodiments of CAD systems and methods according to the invention, which are based on the framework of FIG. 1, will be discussed with reference to FIGS. 2, 3 and 4, for example, for providing assistance to physician workflow in breast imaging. The exemplary embodiments of FIGS. 2 and 3 depict CAD systems and methods for breast imaging for one or more ultrasound imaging modalities. FIG. 4 is an exemplary embodiment of a CAD system which incorporates the systems of FIGS. 2 and 3 and provides further functionality for enabling a multi-modal CAD system that can be used for various for breast imaging in multiple imaging modalities.

Referring now to FIG. 2, a block diagram illustrates a system for providing automatic diagnostic and decision support for breast imaging according to another exemplary embodiment of the invention. In particular, the CAD system (20) of FIG. 2 illustrates one or more exemplary frameworks for implementing the CAD system (10) of FIG. 1 to support ultrasound (B-mode analysis) breast imaging. In general, the CAD system (20) comprises a data processing system (21) which comprises a feature extraction module (22), a feature combination module (23), a classification module (24), a diagnostic/workflow assistance module (25) and an automated detection module (29).

The automated detection module (29) implements methods for processing ultrasound image data (3) of breast tissue to detect and segment potential lesions in the imaged breast tissue. More specifically, the automated detection module (29) implements one or more conventional methods for processing ultrasound image data (3) to automatically detect lesions and other abnormal anatomical structures such as micro calcifications or masses in breast tissue, etc. The automated detection module (29) automatically detects and mark regions of features of interest in the image data, which are identified as being potential lesions, abnormalities, disease states, etc.

The feature extraction module (22) implements various methods (22-1, 22-2, 22-3, 22-4) for extracting relevant parameters from ultrasound image data (3) and other sources of non-image patient data (4) such as clinical, family, history data, etc, such as described in further detail below, which can be used for providing automated diagnosis and decision support functions. The feature combination module (23) combines the extracted features in a manner that is suitable for input to the classification module (24) for analysis.

The classification module (24) comprises a classification method (24-1) (or classification engine) that analyzes the combined extracted parameters using one or more classification models, which are trained/dynamically adapted via model builder (24-2), to generate information that is used to provide diagnostic and decision support. The diagnostic/workflow assistance module (25) includes one or more methods for implementing functions such as described above with reference to FIG. 1 (e.g., providing a diagnosis, providing a set of cases similar to a current case, providing a score showing the likely benefit of additional tests or features that would improving the confidence of diagnosis, etc.).

The CAD system (20) further comprises a user interface (26) (e.g., graphical user interface displayed on computer monitor with keyboard and mouse input devices) which enables a user to select one or more functions supported by the diagnostic/workflow assistance module (25) and which enables the system to render and present processing results to the user. The processing results can be rendered and presented to a user in one or more of various ways according to exemplary embodiments of the invention as described below.

The CAD system (20) further comprises a repository (27) that maintains a clinical domain knowledge base of information that is derived from various sources. For instance, the clinical domain knowledge (27) may include knowledge that is learned or automatically extracted from a large database of analyzed/labeled cases (28) related to the clinical domain(s) supported by the CAD system (20). The clinical domain knowledge (27) may include expert clinical knowledge that is input directly by an expert from analyzing previous claims, or information related to rules/regulations/guidelines associated with medical bodies or insurance companies, with regard to the supported clinical domain(s). As explained in detail below, the clinical domain knowledge in repository (27) can be used by the various methods (22, 23, 24, and 25) of the data processing system (21).

The feature extraction module (22) includes various methods to extract image parameters associated with the "detected" regions of the ultrasound image data, which can be used diagnosing potential cancerous tissue. Such features include parameters associated with speculation (22-1), acoustic shadowing (22-2), height/depth ratio (22-3) and/or other possible image parameters that can be used to automatically classify lesions or abnormalities in breast tissue.

In other exemplary embodiments of the invention, the data processing system (21) extracts and analyzes relevant parameters from non-image patient data records (4) of a subject patient, which can used in conjunction with the extracted image parameters (22-1, 22-3, 22-3) to provide automated diagnosis. The patient data (4) can include patient information from a plurality of structured and unstructured data sources, which is collected over the course of a patient's treatment. In general, the structured data sources include, for example, financial (billing), laboratory, and pharmacy databases, wherein patient information in typically maintained in database tables. The unstructured data sources include for example, waveform data, free-text based documents of laboratory test results, doctor progress notes, details about medical procedures, prescription drug information, radiological reports, and other specialist reports.

The non-image patient data (4) can include a significant amount of useful data indicative of a person having breast cancer or a history that indicates that the person has a high potential for developing breast cancer. By way of example, such clinic information may be found in history and physical notes, wherein a physician notes that a person has been previously diagnosed with breast cancer. Other indications, such as family history of breast cancer, history of smoking, age, gender, etc., can also be used to assess the risk of developing or having breast cancer. Accordingly, the feature extraction module (22) includes one or more data extraction methods (22-4) for extracting relevant patient data from the non-image patient data (4), which may be relevant for assessing or diagnosing a medical condition.

It is to be appreciated than any suitable data analysis/data mining methods may be implemented by the extraction module(s) (22-4) for extracting relevant parameters from the patient data (4). In one exemplary embodiment of the invention, patient data extraction methods (22-4) and feature combination method (23) may be implemented using the data mining methods and feature combination methods as described in commonly assigned and copending U.S. patent application Ser. No. 10/287,055, filed on Nov. 4, 2002, entitled "Patient Data Mining", which claims priority to U.S. Provisional Application Ser. No. 60/335,542, filed on Nov. 2, 2001, which are both fully incorporated herein by reference. Briefly, U.S. Ser. No. 10/287,055 describes data mining methods for extracting relevant information from clinical data records using domain-specific knowledge contained in a knowledge base (e.g., in repository (27)), which are represented as probabilistic assertions about the patient at a particular time (referred to as elements) and combining all elements that refer to the same variable (domain-specific criteria) at a given time period to form a single unified probabilistic assertion regarding that variable.

In the exemplary embodiment of FIG. 2, as noted above, the data processing system (22) uses clinical domain knowledge data maintained in the repository (27) to perform the various methods of feature extraction (22), feature combination (23) and model building (24-2). The domain-specific knowledge base (27) may include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies such as the American College of Radiology (ACR). The domain-specific knowledge base (27) may also include institution-specific domain knowledge. For example, this may include information about the data available at a particular hospital, document structures at a hospital, policies of a hospital, guidelines of a hospital, and any variations of a hospital.

The clinical domain knowledge base (27) may be derived from various sources. For instance, the clinical domain knowledge base (27) may include knowledge that is learned from a large database of analyzed/labeled cases (28). In addition, the clinical domain knowledge base (27) may include knowledge that is input by an expert from analyzing previous claims, or from rules and regulations published by an insurance company, for example. The data in the domain knowledge base (27) can be encoded as an input or as programs that produce information that can be understood by the system. As noted above, the domain expert data may be obtained by manual input from a domain expert using an appropriate user interface or the domain expert data may be automatically or programmatically input.

The extraction modules (22-4) can use relevant data in the domain knowledge base (27) to extract relevant parameters and produce probabilistic assertions (elements) about the patient that are relevant to an instant in time or time period. The domain knowledge required for extraction is generally specific to each source. For example, extraction from a text source may be carried out by phrase spotting, wherein a list of rules are provided that specify the phrases of interest and the inferences that can be drawn therefrom. For example, if there is a statement in a doctor's note with the words—"There is evidence of lesions in the left breast"—then, in order to infer from this sentence that the patient has or may have breast cancer, a rule can be specified that directs the system to look for the phrase "lesion," and, if it is found, to assert that the patient may have breast cancer with a some degree of confidence. Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

The methods implemented by the feature combination module (23) can be those described in the above-incorporated patent application. For example, a feature combination method can be a process of producing a unified view of each variable at a given point in time from potentially conflicting assertions from the same/different sources. In various embodiments of the present invention, this is performed using domain knowledge regarding the statistics of the variables represented by the elements.

The model builder (24-2) builds classification models implemented by the classification method (24-1), which are trained (and possibly dynamically optimized) to analyze various extracted features and provide diagnostic assistance and assessment on various levels, depending on the implementation. It is to be appreciated that the classification models may be "black boxes" that are unable to explain their prediction to a user (which is the case if classifiers are built using neural networks, example). The classification models may be "white boxes" that are in a human readable form (which is the case if classifiers are built using decision trees, for example). In other embodiments, the classification models may be "gray boxes" that can partially explain how solutions are derived (e.g., a combination of "white box" and "black box" type classifiers). The type of classification models that are implemented will depend on the domain knowledge data and model building process (24-2). The type of model building process will vary depending on the classification scheme implemented, which may include decision trees, support vector machines, Bayesian networks, probabilistic reasoning, etc., and other classification methods that are known to those of ordinary skill in the art.

The model builder/update process (24-2) uses data in the clinical domain knowledge base (27) to train classification models, and possibly dynamically update previously trained classification models that are implemented by the classification process (24-1). In one exemplary embodiment of the invention, the model builder/update process (24-2) is implemented "off-line" for building/training a classification model that learns to provide proper diagnostic assessments and decisions for workflow assistance. In another exemplary embodiment of the invention, the model builder/update process (24-2) employs "continuous" learning methods that can use the domain knowledge data in repository (27) which is updated with additional learned data derived from newly analyzed patient data or otherwise optimize the classification model(s) associated with the relevant condition. Advantageously, a continuous learning functionality adds to the robustness of the CAD system (20) by enabling the classification process (24-1) to continually improve over time without costly human intervention.

The diagnostic/workflow assistance module (26) can provide one or more diagnostic and decision support functions as described above with reference to FIG. 1. For instance, the diagnostic/workflow assistance module (26) can command the classification module (24) to classify one or more breast lesions detected in ultrasound image data (4) as malignant or benign and provide a probability of such diagnosis and (optionally) a measure of confidence in the diagnosis, based on a set of features extracted from ultrasound image data (3) and/or non-image patient data records (4). The classification engine (25-1) could perform such classification using one or more classification models that are trained to analyze the combined features output from module (23). In another exemplary embodiment, the diagnostic/workflow assistance module (25-1) can command the classification module (24) to determine what additional image parameter or features (e.g., from B-mode ultrasound image data, other image mode, and/or non-image data) can be obtained and further analyzed to increase the confidence in the diagnosis. Moreover, the diagnostic/workflow assistance module (25-1) can command the classification module (23) to obtain and display (via user interface) one or more similar patient cases in repository (27) based on the current set of extracted features.

Referring now to FIG. 3, a block diagram illustrates a system for providing automated diagnostic and decision support for breast imaging according to another exemplary embodiment of the invention. More specifically, FIG. 3 illustrates a CAD system (30) that supports additional ultrasound imaging methods (in addition to B-mode analysis) for providing automated diagnosis of breast lesions in breast tissue, for example, and other decision support function to assist physician workflow. In one exemplary embodiment, the CAD system (30) of FIG. 3 incorporates an automated B-mode analysis of the CAD system (20) discussed above with reference to FIG. 2. The CAD system (30) of FIG. 3 illustrates one or more exemplary frameworks for the CAD system (10) of FIG. 1 to support one or more ultrasound imaging methods including, for example, B-mode, contrast imaging, and/or strain imaging, etc.

More specifically, referring to FIG. 3, the CAD system (30) comprises a data processing system (31) which implements methods for automatic classification (diagnosis) of breast cancer based on various parameters are extracted from one or more types of ultrasound image data (5) and/or non-image patient data (6), as well as other methods to assist a physician to decide an a care or diagnosis path for a particular patient. In general, the data processing system (31) comprises a feature extraction module (32), a feature combination module (33), a classification module (34) and a diagnostic/workflow assistance module (35). Moreover, the CAD system (30) comprises a user interface (36) which enables user interaction with the CAD system (30) to select one or more functions supported by the diagnostic/workflow assistance module (35) (e.g., providing automated diagnosis and confidence of diagnosis for breast cancer, determine what additional ultrasound imaging modalities or features (e.g., from B-mode ultrasound image data, other image mode, and/or non-image data) can be obtained and further analyzed to increase the confidence in diagnosis, obtain and display one or more similar patient cases in a repository (38) based on the current set of extracted features.)

The feature extraction module (32) implements various methods (32-1~32-5) for extracting relevant parameters from one or more of various modes of ultrasound image data (5) and non-image patient data (6), which can be analyzed to provided automated diagnosis and other types of decision support as discussed herein. For instance, the feature extraction module (32) includes an automated B-mode analysis module (32-1) which implements, for example, the automated detection (29), speculation (23-1), acoustic shadowing (23-2), and H/D ratio (23-3) methods as described above in the system (20) of FIG. 2. In addition, the feature extraction module (32) includes methods for extracting relevant parameters from ultrasound measurements including strain and elastography (32-2), motion of fluid using techniques such as acoustic streaming (32-3), 3D ultrasound imaging (32-4) and motion of blood using techniques such as contrast perfusion (32-5).

The various feature extraction modules can be implemented using methods that are well known to those of ordinary skill in the art. For example, for ultrasound strain/elastography imaging, the systems and method described in the following patents: Hall et al, "Ultrasonic elasticity imaging", U.S. Pat. No. 6,508,768, issued Jan. 21, 2003; Nightingale et al, "Method and apparatus for the identification and characterization of regions of altered stiffness", U.S. Pat. No. 6,371,912, issued Apr. 16, 2002; and Von Behren et al, "System and method for strain image display", U.S. Pat. No. 6,558,424, issued May 6, 2003, which are all incorporated herein by reference, can be implemented for extracting relevant parameters from ultrasound measurements including strain and elastography. Moreover, the systems and methods for acoustic streaming as described in Trahey et al, "Method and apparatus for distinguishing between solid masses and fluid-filled cysts", U.S. Pat. No. 5,487,387, issued Jan. 30, 1996, which is incorporated herein by reference, can be used for extracting features related to motion of fluid. In addition, the systems and methods for contrast perfusion as described in Philips et al, "Dual process ultrasound contrast agent imaging", U.S. Pat. No. 6,632,177, issued Oct. 14, 2003, which is incorporated herein by reference, may be used for extracting features related to motion of blood. It is to be understood that other known techniques may be implemented.

The feature combination module (33) combines a set of extracted features in a manner that is suitable for input and analysis by the classification module (34). The classification module (34) comprises classification methods (34-1) to analyze the combined extracted parameters using one or more classification models, which are trained/dynamically adapted via model builder (34-2), to provide automatic diagnosis of breast cancer and other decisions support functions. The CAD system (30) further comprises a repository (37) that maintains a clinical domain knowledge base of information which provides training data used by the model builder (34-2) to build/train classification models used by the classification methods (34-1). A large database of analyzed/labeled cases (38) related to the clinical domain or domains supported by the CAD system (30) can be used to obtain training data in repository (37). The clinical domain knowledge in repository (37) can be used by the various methods (32, 33, 34 and 35) of the data processing system (31).

In general, the various components of the CAD system (30) of FIG. 3 are essentially similar to those of the CAD system (20) of FIG. 2 as discussed above, except that the CAD system (30) of FIG. 3 provides a more diverse framework that supports various ultrasound imaging methods in addition to B-mode ultrasound to enable a more complete CAD system for ultrasound breast imaging. It is to be appreciated that the various modules (32, 33, 34 and 35) in FIG. 3 can implement the same or similar methods as those corresponding modules (22, 23, 24 and 25) of the CAD system (20) of FIG. 2 as described above. However, the various methods, such as the classification and model building methods in classification modules (24) and (34) will vary depending on the types of decision support functions, feature extraction methods and/or image modalities supported by the respective CAD systems (20) and (30). Moreover, the clinical domain knowledge base (37) is similar to the knowledge base (27) of FIG. 2, except that the training data in knowledge bases (27) and (37) will vary depending on the types of decision support functions, feature extraction methods and/or image modalities supported by the respective CAD systems (20) and (30).

Referring now to FIG. 4, a block diagram illustrates a system for providing automated diagnostic and decision support for breast imaging according to another exemplary embodiment of the invention. More specifically, in one exemplary embodiment of the invention, FIG. 4 illustrates a CAD system (40) that is an extension of the exemplary CAD systems (20) and (30), wherein the CAD system (40) incorporates the functions and methods of CAD systems (20) and (30) for ultrasound breast imaging, and further incorporated methods and functions for enabling a multi-modal CAD for breast imaging in multiple imaging modalities.

Referring to FIG. 4, the CAD system (40) comprises a data processing system (41) which implements methods for providing automated diagnosis of breast lesions in breast tissue and providing decision support for diagnostic and/or care paths to assist physician workflow, by extracting and analyzing parameters from various sources of patient information (7), including, for example, one or more different types of image data (e.g., MRI image data (7a), ultrasound image data (7b), X-Ray mammography image data (7c) and non-image data such as genetics and/or proteomics data (7d) and clinical, history and/or physical data (7e) of the subject patient.

In general, the data processing system (41) comprises a feature extraction module (42), a feature combination module (43), a classification module (44) and a diagnostic/workflow assistance module (45). Moreover, the CAD system (40) comprises a user interface (46) which enables user interaction with the CAD system (40) to select one or more functions supported by the diagnostic/workflow assistance module (45) (e.g., providing automated diagnosis and confidence of diagnosis for breast cancer, determining what additional imaging modalities or features could be obtained and further analyzed to increase the confidence in diagnosis, obtaining and displaying one or more similar patient cases in a repository based on a current set of extracted features, etc.)

The feature extraction module (42) implements "n" feature extraction methods for extracting image parameters (42-1~42-2) from the supported imaging modalities, and other feature or text extraction methods (42-3, 42-4) for extracting parameters from non-image data sources. For instance, the feature extraction module (42) can include methods for extracting and analyzing image parameter from various types of ultrasound data (as discussed above with reference to FIGS. 2 and 3) and other imaging modalities. The feature combination module (43) combines a set of extracted features in a manner that is suitable for input and analysis by the classification module (44). The classification module (44) comprises classification methods (44-1) to analyze the combined extracted parameters using one or more classification models, which are trained/dynamically adapted via model builder (44-2), to provide the various decision support functions. The CAD system (40) further comprises a repository (47) that maintains a clinical domain knowledge base of information which provides training data used by the model builder (44-2) to build/train classification models used by the classification methods (44-1). A large database of analyzed/labeled cases (48) related to the clinical domain or domains supported by the CAD system (40) can be used to obtain training data that is stored in the repository (47). The clinical domain knowledge in repository (47) can be used by the various methods (42, 43, 44 and 45) of the data processing system (41).

It is to be appreciated that the various modules (42, 43, 44 and 45) in FIG. 4 can implement the same or similar methods as those corresponding modules (22, 23, 24 and 25) of the CAD system (20) of FIG. 2 and/or corresponding modules (32, 33, 34 and 35) of the CAD system (30) of FIG. 3, as described above. However, the various methods, such as the classification and model building methods of the classification module (44) will vary depending on the types of decision support functions, feature extraction methods and/or image modalities supported by the CAD system (40). Moreover, the clinical domain knowledge base (47) is similar to the knowledge bases (27) and (37) of FIGS. 2 and 3, except that the training data in knowledge bases (47) will vary depending on the types of decision support functions, feature extraction methods and/or image modalities supported by the CAD system (40).

Figure 5:
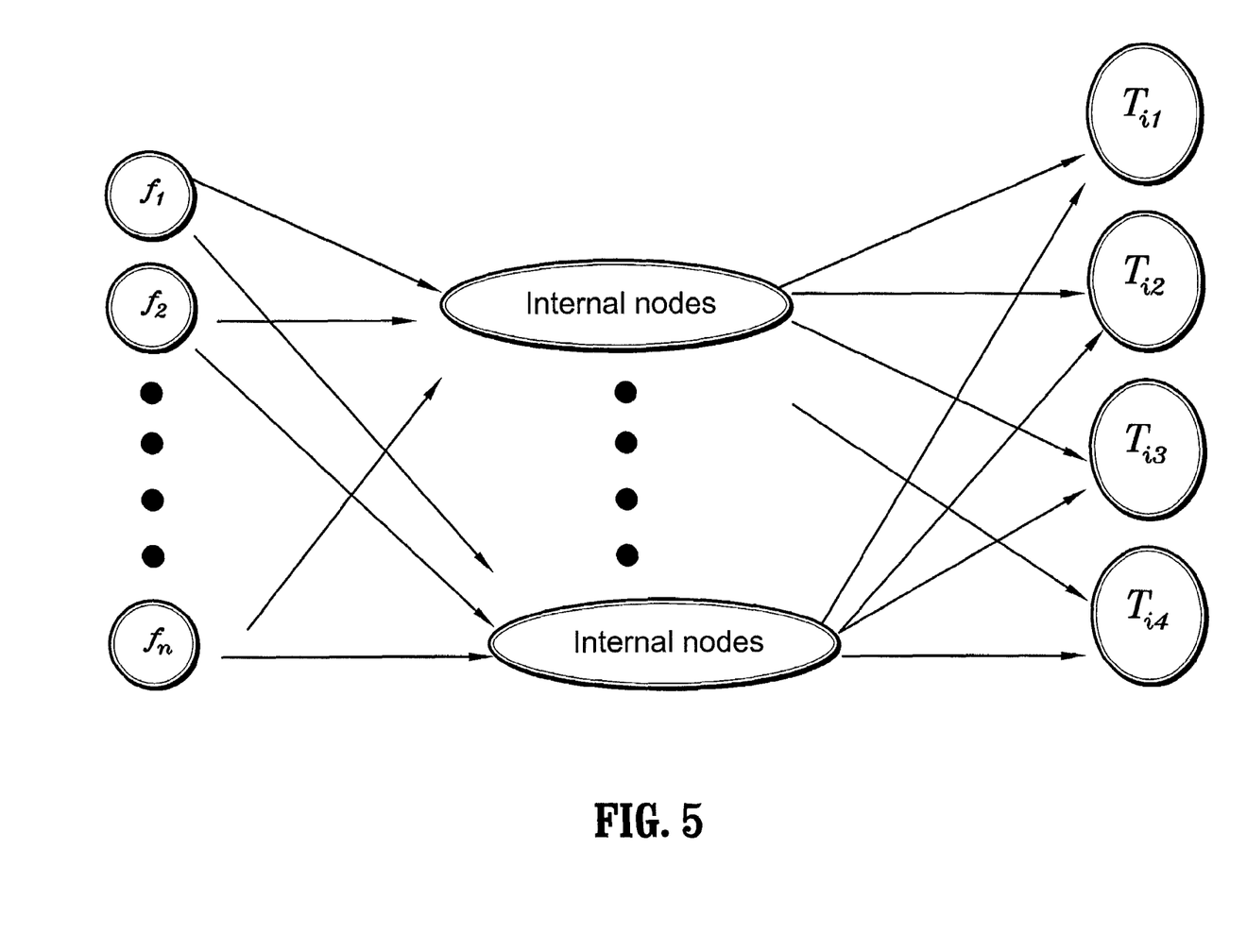
FIG. 5 is an exemplary diagram illustrating a classification method according to an exemplary embodiment of the invention.

Various machine learning methods according to exemplary embodiments of the invention for assessing the likely value of additional tests for diagnosis of breast cancer will now be described with reference to the exemplary node diagram of FIG. 5. For these exemplary embodiments, it is assumed that a training set consists of m cases and each case consists of n features extracted from previously performed tests. Each case $C_i$, (i=1, . . . , m) can be represented as a vector of features ($f_1$, $f_2$, . . . , $f_n$).

It is further assumed that for each case $C_i$, the real diagnosis ($d_i$) given by a biopsy result is:

$$d_i = \begin{cases} 1 & \text{If a lesion is malignant} \\ 0 & \text{Otherwise} \end{cases}$$

and that there are k variables corresponding to the different tests that were performed on the patients ($T_{i1}$, $T_{i2}$, $T_{i3}$, . . . $T_{ik}$), wherein each one of the k variables can take values in the set {0,1}, and wherein k=1 if the corresponding test predicted correctly with respect to the real diagnosis $d_i$, or where k=0 otherwise.

Further assuming that such previous information is extracted from the training data, the exemplary machine learning based methods described hereafter can be used to predict which test will provide an accurate diagnosis based on a feature vector extracted from a patient medical history.

In one exemplary embodiment, one method is as follows. First, a mapping M is determined from the feature space to {($P_1$, $P_2$, $P_3$, $P_4$)/$P_i \in \{0,1\}$} such that for every $C_i$, $M(C_i)=M$ ($f_1$, $f_2$, . . . , $f_n$)=($T_{i1}$, $T_{i2}$, $T_{i3}$, $T_{i4}$). This process can be achieved using artificial neural network techniques as illustrated in FIG. 5. For each new patient, the mapping M will provide a corresponding binary output that describes which tests are recommended for this patient.

This problem also can be viewed as a multi-class classification problem where for each case $C_i$, its label is defined according to which test gave the correct diagnosis. For example, one possible approach is as follows. For each test, all the training cases are labeled according to the accuracy of that test for that case. Then, four classifiers are trained (one for each test) using any binary classification algorithm (e.g., SVMs, Decision Trees, Bayesian networks, etc.). When a new patient is considered, the patient data is tested in the four classifiers to predict which tests will give the correct diagnosis.

It is to be noted that with the above two approaches, the outcome of the process can be more than one test.

Another exemplary approach is as follows. Assume that there are m cases in a training set. A new case will be compared to these m cases using the n features described above. Based on this comparison, p cases are selected as being most "similar" to the current case, wherein similarity can be defined in one of various ways. For instance, one approach is to consider the Euclidean distance in the n-dimensional feature space. Other well-known distance measures can also be employed. It is to be appreciated that the above process can also be used to select exemplar cases from a library of cases for display as well.

One the similarity measures are determined and the most "similar" cases are identified, classifiers can be constructed for each of the k tests in the training set. In particular, by way of example, a classifier would be constructed to test whether a lesion is benign or malignant using, for example, each of the following sets of information: (i) current information and a diagnostic mammogram; (ii) current information and ultrasound; (iii) current information and MRI, etc.

Each classifier would be constructed without learning from one of the p cases (i.e. leave-one-out approach), and then the withheld case would be classified using this classifier. This would be repeated for each of the p cases, and the entire process for each of the k tests. An average likelihood would then be computed for each of the k tests, which would serve as the score of which test would be most useful.

It is to be appreciated that in accordance with other exemplary embodiments of the invention, CAD systems may be implemented in a distributed model, wherein various modules/components of the CAD are distributed over a communications network. For example, a CAD system can be offered by an ASP (application service provider) to provide remote access serving of CAD functions via an application server. For example, a database of cases used to identify similar cases could be located in a central location. The advantage is that large databases of cases, which occupy a lot of memory, do not have to reside at every system. In addition, updates to the cases can be made very easily. This central location could be within a hospital, for example, or it could be one central database accessed by everyone using such a system. Another possibility is to use a distributed database, where cases are located in multiple locations but are searched and accessed as if they are in one place. That way, cases located at different locations can be searched to find similar cases. In addition to the database, the other parts of the CAD system, such as the classifier, could be centrally located.

Moreover, in view of above, it is to be appreciated that a CAD system according to the invention can be implemented as a service (e.g., Web service) that is offered by a third-party service provider pursuant to service contract or SLA (service level agreement) to provide diagnostic support and other decision support functions as described herein based one of various service/payment schemes. For example, the third-party service provider can be contractually obligated to train, maintain, and update classification models for various clinical domains, and a physician or healthcare organization can access the CAD system "on-line" on a pay-per use basis, yearly subscription fee, etc. In such instance, various methods known to those of ordinary skill in the art can be implemented to maintain patient confidentiality and otherwise transmit patient data over communication channels using secured encryption, compression schemes, etc. Those of ordinary skill in the art can readily envision various architectures and implementation for CAD systems according to the invention and nothing herein shall be construed as a limitation of the scope of the invention.

Although exemplary embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for providing automatic diagnosis and decision support for breast imaging in an imaging process apparatus, comprising:
    obtaining information from image data of abnormal breast tissue of a subject patient;
    obtaining information from non-image data records of the subject patient by extracting the non-image information from an unstructured free-text source using phrase spotting; and
    automatically diagnosing the abnormal breast tissue using the obtained information from image data and the extracted non-image information.

2. The method of claim 1, wherein obtaining information from image data comprises automatically extracting one or more features from ultrasound image data, which are to be used for automatically diagnosing the abnormal breast tissue.

3. The method of claim 2, wherein the ultrasound data is 3D ultrasound data.

4. The method of claim 2, further comprising automatically detecting the abnormal breast tissue in the ultrasound image data prior to automatically extracting.

5. The method of claim 2 wherein automatically extracting one or more features from ultrasound image data comprises extracting features related to one of spiculation acoustic shadowing, or height/depth ratio of the abnormal breast tissue, and any combination of said features.

6. The method of claim 2, wherein automatically extracting one or more features from ultrasound image data comprises extracting features related to one of acoustic, elastic, perfusion or 3D features of the abnormal breast tissue, or any combination of said features.

7. The method of claim 2, wherein the image data comprises one of ultrasound image data, X-ray mammography image data, MRI image data, and a combination thereof.

8. The method of claim 1, wherein automatically diagnosing the abnormal breast tissue comprises automatically determining a probability of diagnosis.

9. The method of claim 1, further comprising automatically identifying one or more previously diagnosed cases that are similar to a current diagnosis.

10. The method of claim 1, wherein automatically diagnosing the abnormal breast tissue using the obtained information comprises classifying the abnormal breast tissue using a machine learning method, a model-based method, or any combination of machine learning and model-based methods, that is trained to analyze the obtained information.

11. The method of claim 8, further comprising automatically determining a confidence of said probability of diagnosis.

12. The method of claim 11, further comprising automatically determining additional information which would increase the confidence of said probability of diagnosis.

13. The method of claim 12, wherein automatically determining additional information further comprises determining a measure of usefulness of said additional information in increasing said confidence of diagnosis.

14. The method of claim 9, wherein automatically identifying one or more previously diagnosed cases that are similar to a current diagnosis comprises using the obtained information to search a library of labeled cases with features similar to the obtained information.

15. The method of claim 14, comprising displaying the identified cases.

16. The method of claim 10, comprising retraining the method for classifying on a continual or periodic basis using expert data and/or data learned from a plurality of case studies.

17. A method for providing automatic diagnosis and decision support for breast imaging in an imaging process apparatus, comprising:
    obtaining information from ultrasound image data of abnormal breast tissue of a subject patient;
    obtaining information from non-image data records of the subject patient by extracting the non-image information from an unstructured free-text source using phrase spotting;
    automatically extracting features from the ultrasound image data, the extracted features comprising at least two of strain, fluid motion, blood motion, and B-mode images wherein the ultrasound image data comprises 3D ultrasound image data and further comprising extracting features from the 3D ultrasound image data; and
    automatically diagnosing the abnormal breast tissue using the extracted features and the extracted non-image information.

18. A method for providing automated diagnostic and decision support for medical imaging in an imaging process apparatus, comprising:
    automatically extracting features from patient data of a subject patient, the patient data comprising image data and non-image data, wherein extraction of non-image data is performed from an unstructured free-text source using phrase spotting; and
    automatically determining a current state of the subject patient by analyzing the features extracted from the patient data of the subject patient; and
    automatically providing decision support to assist physician workflow regarding a healthcare or diagnostic or therapeutic path for the subject patient, based on a determined current state of the subject patient.

19. The method of claim 18, wherein automatically determining a current state of the subject patient comprises automatically determining a probability of diagnosis of breast cancer or the probability of developing breast cancer in the future.

20. The method of claim 19, wherein automatically providing decision support comprises automatically determining one or more additional imaging methods that would increase a confidence of said probability of diagnosis of breast cancer.

21. The method of claim 19, wherein automatically providing decision support comprises automatically identifying one or more previously diagnosed cases that are similar to the current case.

22. The method of claim 18, wherein automatically determining a current state of the subject patient comprises automatically determining a likelihood of the subject patient developing breast cancer.

23. The method of claim 18, wherein automatically providing decision support comprises automatically determining one or more diagnostic imaging screening tests that could be given to the subject patient for detecting breast cancer or provide a better assessment of the likelihood of the subject patient developing breast cancer.

24. The method of claim 18, wherein automatically determining a current state of the subject patient comprises automatically assessing characteristics and location of a breast tumor.

25. The method of claim 24, wherein automatically providing decision support comprises automatically determining one or more diagnostic imaging tests that could be used for staging the lesion.

26. The method of claim 18, wherein automatically providing decision support to assist a physician workflow comprises suggesting a therapy.

27. The method of claim 19, wherein automatically providing decision support comprises automatically determining one or more additional features which would increase a confidence of said probability of diagnosis of breast cancer.

28. The method of claim 20, wherein automatically determining one or more additional imaging methods further comprises determining for each of said one or more additional imaging methods, a measure of usefulness in increasing said confidence of diagnosis.

29. The method of claim 21, comprising displaying the identified cases.

30. The method of claim 25, wherein automatically determining one or more diagnostic imaging tests that could be used for staging the lesion further comprises providing a measure of usefulness for each of the diagnostic imaging tests.

31. The method of claim 25, wherein automatically providing decision support comprises automatically identifying one or more previous staging cases that are similar to a current case.

32. The method of claim 26, further comprising automatically providing a probability and/or measure of confidence that the therapy will have a determined outcome.

33. The method of claim 26, further comprising automatically providing a probability and/or measure of confidence that the therapy will not have a determined detrimental impact such as side effects.

34. The method of claim 27, wherein automatically determining one or more additional features further comprises determining for each of said one or more additional features, a measure of usefulness in increasing said confidence of diagnosis.

35. The meth of claim 31, further comprising displaying the identified staging cases.

36. The method of claim 26, wherein the probability is a distribution over possible outcomes both beneficial and detrimental.

37. The method of claim 36, wherein the probability is a set of distributions over possible outcomes both beneficial and detrimental at one or more time points in the future.

38. The method of claim 36, wherein the probability is a time-varying distribution over possible outcomes at different times in the future.

* * * * *